US006482206B2

(12) United States Patent
Schoenefeld

(10) Patent No.: US 6,482,206 B2
(45) Date of Patent: Nov. 19, 2002

(54) METHOD AND APPARATUS FOR EXTERNAL FIXATION OF BONES

(75) Inventor: Ryan J. Schoenefeld, Fort Wayne, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/790,770

(22) Filed: Feb. 22, 2001

(65) Prior Publication Data

US 2002/0115998 A1 Aug. 22, 2002

(51) Int. Cl.[7] .................................................. A61F 5/04
(52) U.S. Cl. .............................. 606/59; 606/54; 606/56
(58) Field of Search ............................. 606/53, 54, 55, 606/56, 57, 58, 59

(56) References Cited

U.S. PATENT DOCUMENTS

| | | | | |
|---|---|---|---|---|
| 4,483,334 A | * | 11/1984 | Murray .......................... 606/54 |
| 4,662,365 A | | 5/1987 | Gotzen et al. ......... 128/92 ZW |
| 4,848,368 A | | 7/1989 | Kronner ................. 128/92 ZW |
| 5,108,394 A | | 4/1992 | Kurokawa et al. ............. 606/59 |
| 5,403,313 A | | 4/1995 | Lin ............................... 606/54 |
| 5,443,464 A | * | 8/1995 | Russell et al. ................. 606/54 |
| 5,630,815 A | | 5/1997 | Pohl et al. ..................... 606/59 |
| 5,683,389 A | | 11/1997 | Orsak .......................... 606/59 |
| 5,690,633 A | | 11/1997 | Taylor et al. .................. 606/73 |
| 5,769,851 A | * | 6/1998 | Veith ............................ 606/57 |
| 5,797,908 A | | 8/1998 | Meyers et al. ................ 606/54 |
| 5,891,144 A | | 4/1999 | Mata et al. .................... 606/59 |
| 5,921,985 A | | 7/1999 | Ross, Jr. et al. ............... 606/59 |
| 6,022,348 A | * | 2/2000 | Spitzer ......................... 606/54 |
| 6,102,911 A | | 8/2000 | Faccioli et al. ............... 606/54 |
| 6,217,577 B1 | * | 4/2001 | Hofmann ...................... 606/57 |

* cited by examiner

*Primary Examiner*—Pedro Philogene
(74) *Attorney, Agent, or Firm*—Harness, Dickey & Pierce, P.L.C.

(57) ABSTRACT

An external fixator for securing a first bone portion in a fixed relationship with respect to a second bone portion includes a longitudinally extending rod and a bone screw clamping assembly. The bone screw clamping assembly receives at least one bone screw. The bone screw clamping assembly is mounted to the rod for relative universal movement about a point through which the rod passes and is normally permitted to longitudinally translate along an axis defined by the rod.

24 Claims, 5 Drawing Sheets

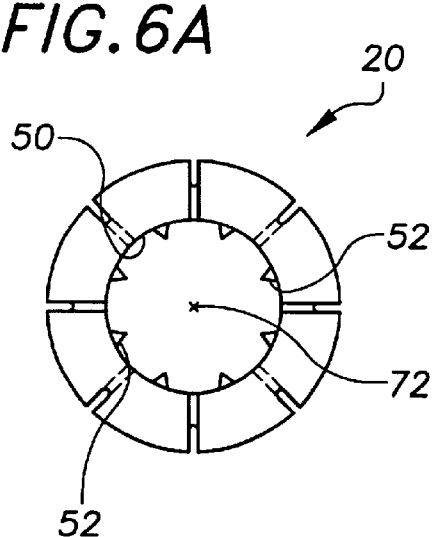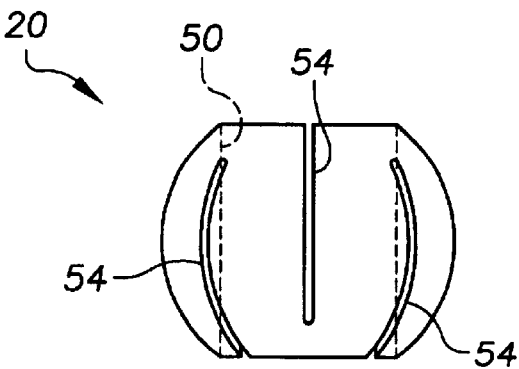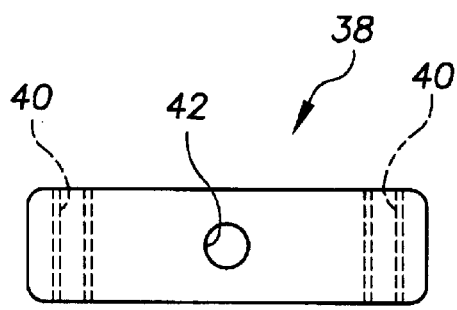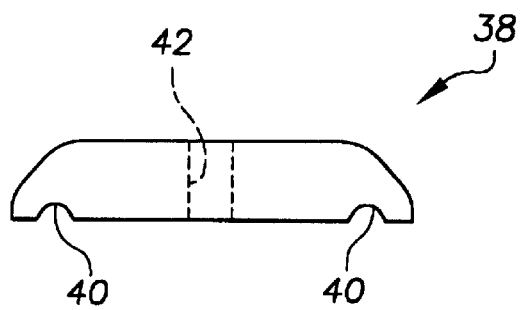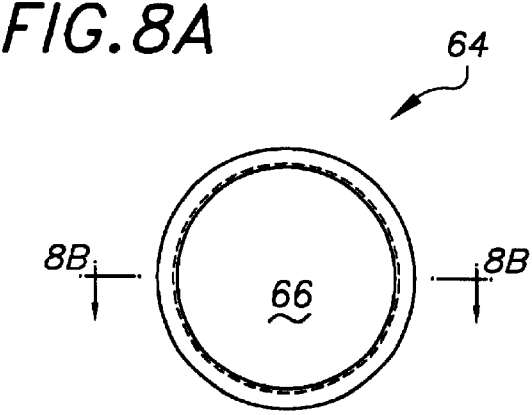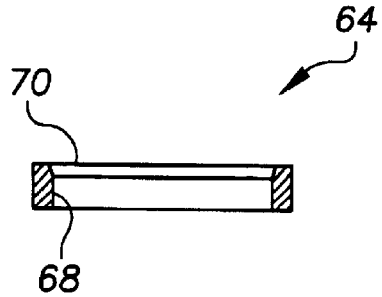

METHOD AND APPARATUS FOR EXTERNAL FIXATION OF BONES

FIELD OF THE INVENTION

The present invention relates generally to orthopedic surgical procedures, and more particularly to a method and apparatus for an external fixation of bones.

BACKGROUND OF THE INVENTION

In various orthopedic surgical procedures, it is necessary to secure two or more portions of bone in a relatively fixed relationship to each other. This need is often a result of a fracture which has occurred to the bone. To ensure that the bone can properly regenerate and fuse the fractures of the bone, it is important that the various bone portions be fixed at the desired position during bone regeneration.

Various external fixation devices for the repair of traumatized bone are known. For example, U.S. Pat. No. 5,620,442 to Bailey et al. discloses an apparatus for the external fixation of small bones. The apparatus is illustrated to include a first bone screw clamp for receiving a first bone screw which is connected to a first bone portion. The external fixator further includes a second bone screw clamp which is operable to receive a second bone screw connected to the second bone portion. The first and second bone screw clamps both include a spherical portion. The external fixator further includes a connection member for securing the spherical portions of the bone screw clamps. The connection member defines a radiographic window to permit radiographic examination of the bone fracture without removing the apparatus. U.S. Pat. No. 5,620,442 is hereby incorporated by reference as if fully set forth herein.

While known fixators, including the type described above, have proven to be effective in fixating bones, they nevertheless can be the subject of certain improvements for particular external fixation applications.

SUMMARY OF THE INVENTION

According to one aspect, the present invention relates to a fixator operable for securing two portions of bone in a fixed relationship to each other, with the first bone portion having a first bone screw attached thereto and the second bone portion having a second bone screw attached thereto. The fixator generally includes a bone screw clamp assembly having a base and a cap member that define a cavity receiving a compressible spherical member. A connecting rod passes through the spherical member. Selected movement of the cap member relative to the base arrests relative movement between the pin clamp assembly and the connecting rod.

One particular advantage of the present invention is the provision of a method and apparatus for the external fixation of bones that allows universal adjustment of a bone screw clamp assembly about a point through which a connecting rod passes.

Further areas of applicability of the present invention will become apparent from the detailed description provided hereinafter. It should be understood that the detailed description and specific examples, while indicating the preferred embodiment of the invention, are intended for purposes of illustration only and are not intended to limited the scope of the invention.

BRIEF DESCRIPTION OF THE DRAWINGS

The present invention will become more fully understood from the detailed description and the accompanying drawings, wherein:

FIGS. 6(A)–6(B) are views of a spherical member of the apparatus for external fixation of bones shown in FIG. 1 according to the teachings of the preferred embodiment of the present invention.

FIGS. 7(A)–7(B) are views of a pin clamp of the first bone screw clamp assembly according to the teachings of the preferred embodiment of the present invention.

FIGS. 8(A)–8(B) are views of one of the rings of the apparatus for external fixation of bones shown in FIG. 1 according to the teachings of the preferred embodiment of the present invention.

DETAILED DESCRIPTION OF THE PREFERRED EMBODIMENTS

The following description of the preferred embodiment of the present invention will be understood to be merely exemplary in nature and is in no way intended to limit the subject invention or its application or uses.

Figure 1:
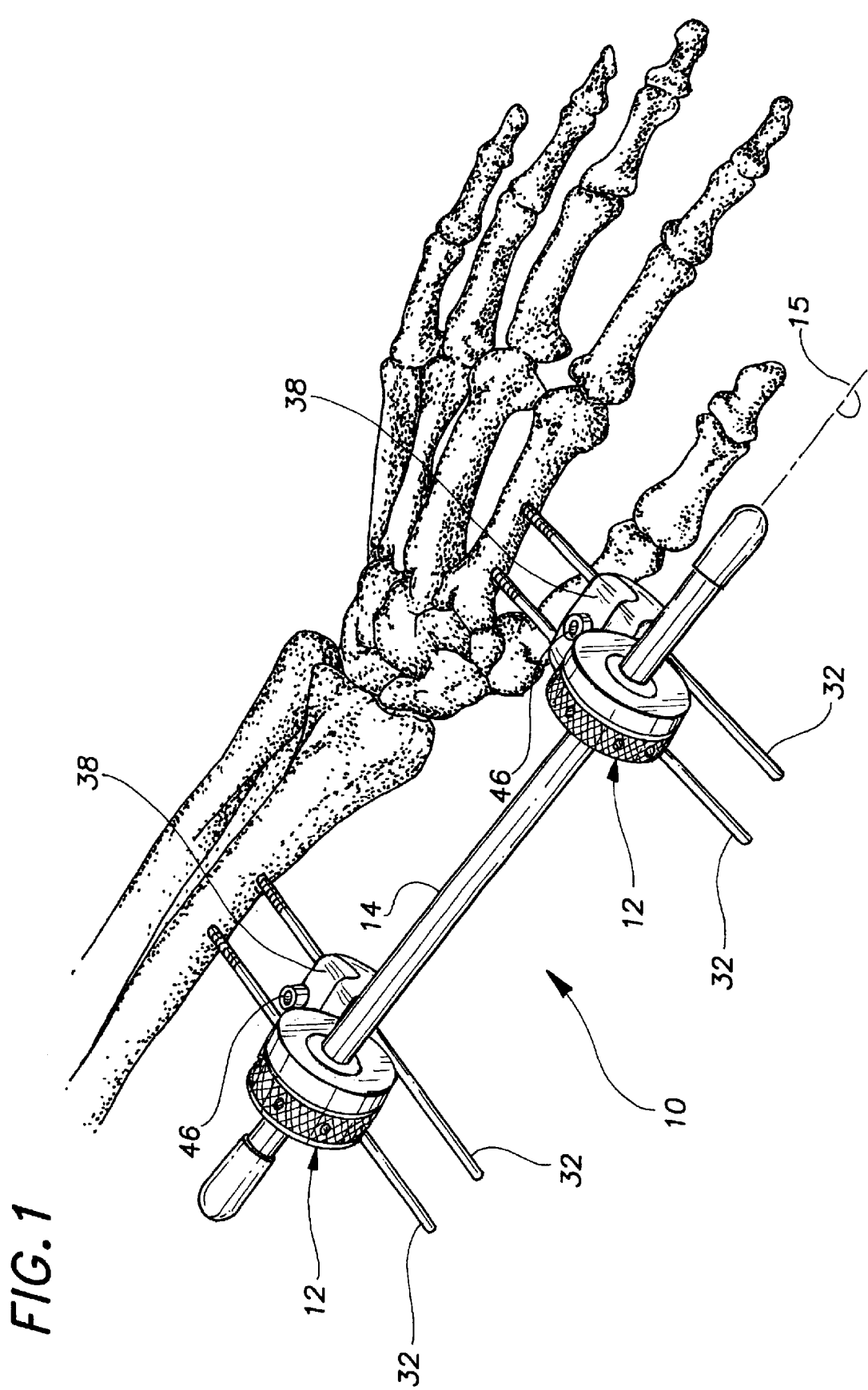
FIG. 1 is a perspective view of the apparatus for external fixation of bones according to the teachings of the preferred embodiment of the present invention shown in operative association with a wrist joint.

Referring initially to FIG. 1, an apparatus 10 for the external fixation of bones is shown constructed in accordance with the teachings of the preferred embodiment of the present invention. In particular, the apparatus 10 is illustrated as being used for securing a bone fracture located in close proximity to the wrist joint such as a Colles fracture. The apparatus 10 is used to secure bone portions in a fixed relationship so as to permit the fractured portions to fuse properly. While the apparatus 10 is shown in the environmental view of FIG. 1 in conjunction with a wrist joint, it will be appreciated that the apparatus 10 may be used for various other external fixation applications.

The construction of the apparatus 10 will now be described with continued reference to FIG. 1 and additional reference to FIGS. 2 through 8B. The apparatus 10 is shown to generally include a pair of bone screw clamp assemblies or clamping assemblies 12 and a connection member 14. In the preferred embodiment, the bone screw clamping assemblies 12 are identical. Further in the preferred embodiment, the connection member 14 is a cylindrical rod that longitudinally extends along an axis 15.

Each of the bone screw clamp assemblies 12 is illustrated to generally include a base 16, a cap member 18 and a spherical member 20. As will become understood more fully below, the base 16 and the cap member 18 cooperate to define a cavity for receiving the spherical member 20. In certain applications, it may be desirable to use three or more bone screw clamp assemblies 12.

With particular reference to FIGS. 4A–4D, the bone screw clamp assembly 12 is shown to define a passage 22 for receiving the longitudinal extending cylindrical rod 14. The passage 22 includes a first cylindrical portion 24 (see FIG. 4D) which defines a portion of the cavity for receiving the spherical member 20 and is generally cylindrical in shape. A second portion 26 of the passage 22 is conical in shape and thereby adapted to accommodate angulation of the longitudinally extending rod 14. An external surface 28 of the bone screw clamp assembly 12 which circumferentially surrounds the first portion 24 of the passage 22 is externally threaded for threadably engaging the cap member 18.

The bone screw clamp assembly 12 is further shown to include a portion 30 for receiving at least one bone screw 32. In the embodiment illustrated, each of the bone screw receiving portions 30 is configured to receive two bone screws 32. However, those skilled in the art will readily appreciated that the bone screw clamping assemblies 12 may be designed to accommodate 1, 3, or more bone screws 32.

The bone screw receiving portion 30 defines a pair of apertures 34 for directly receiving the bone screws 32. The apertures 34 are oriented generally perpendicular to an axis passing through the passage 22. A portion of the bone screw receiving portion 30 is cutaway to provide a seat 36 which intersects both of the apertures 34. As particularly shown in FIGS. 1 and 3, the seat 36 receives a bone screw clamp 38 which secures the pair of bone screws 32 to the portion 30.

The bone screw clamps 38 are shown particularly in FIGS. 7A and 7B to partially define a pair of channels 40 for cooperating with the apertures 34 to receive the bone screws 32. An aperture 42 extends perpendicular to the channels 40 and aligns with a threaded aperture 44 provided in portion 30. These apertures 42 and 44 receive a set screw 46 for securing the bone screw clamp 38 to the portion 30.

With particular reference to FIGS. 6A and 6B, the spherical member 20 of the present invention is shown to include an aperture 50 for receiving the longitudinally extending rod 14. The spherical member 20 is shown to include a plurality of teeth 52 which radially extend in an inward direction toward the longitudinally extending rod 14. The spherical member 20 is further formed to include a plurality of slots 54 which extend generally parallel to the rod 14. The slots 54 each begin adjacent one of the ends of the spherical member 20 as defined by the aperture 50 and extend substantially but not completely across the spherical member 20. Adjacent ones of the slots 54 begin on opposite sides of the spherical member 20. Such a configuration facilitates compressibility of the spherical member 20.

Figure 5A:
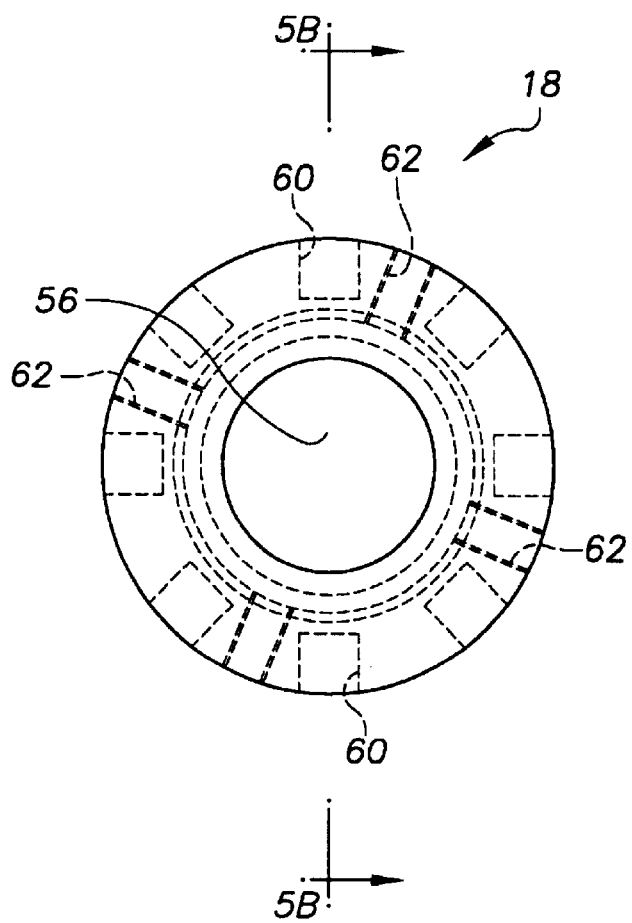
FIGS. 5(A)–5(C) are views of a cap member of the apparatus for external fixation of bones shown in FIG. 1 according to the teachings of the preferred embodiment of the present invention.
Figure 5B:
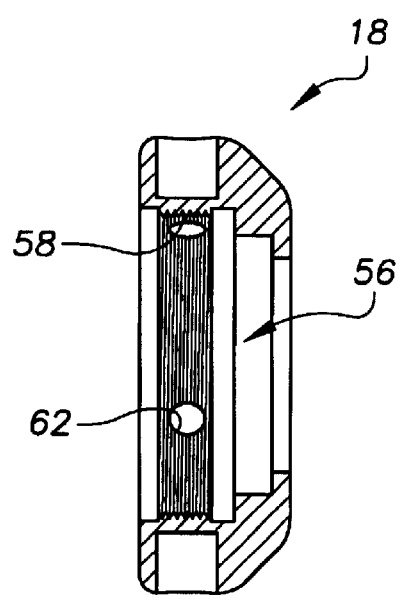
Figure 5C:
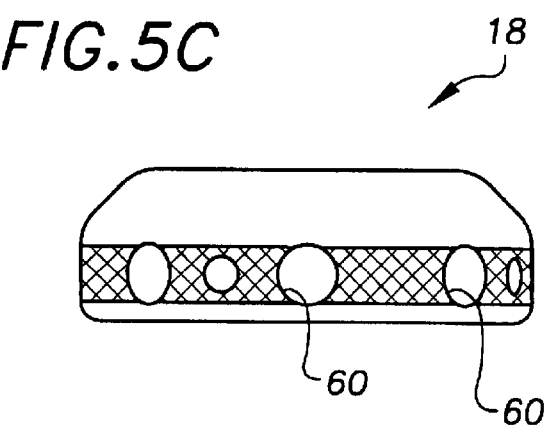

With reference to FIGS. 5A–5C, the cap member 18 is shown to include a passage 56 for receiving the longitudinally extending rod 14. A first portion 58 of the passage 56 is internally threaded for threadably engaging the externally threaded portion of the base 16. The cap member 18 is shown to include a first plurality of radially extending apertures 60 for receiving a tool (not shown) for driving the cap member 18 relative to the base 16. The cap member 18 is further shown to include a second plurality of radially extending apertures 62. The apertures 62 of the second plurality intersect the passage 56 and are each adapted to threadably receive a set screw.

Figure 2:
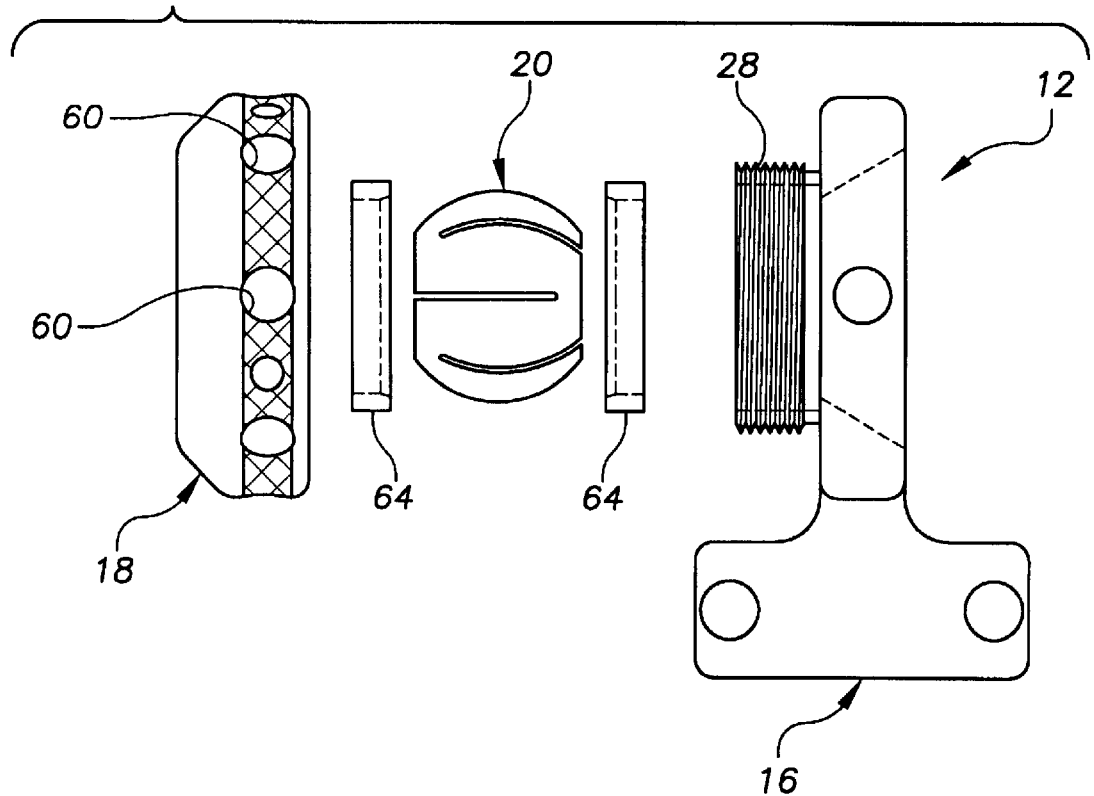
FIG. 2 is an exploded view of a first bone screw clamp assembly of the apparatus for external fixation of bones shown in FIG. 1 according to the teachings of the preferred embodiment of the present invention.

With particular reference to FIGS. 2, 8A and 8B, each of the bone screw clamp assemblies 12 is shown to preferably include a pair of substantially identical rings 64. One of the rings 64 is disposed between the base 16 and the spherical member 20 and the other of the rings 64 is disposed between the cap member 18 and the spherical member 20. In the preferred embodiment, the rings 64 are shown to include an opening 66 including a cylindrical portion 68 and a tapered portion 70. The tapered portion 70 directly engages the spherical member 20. In one application, the rings 64 may be steel. However, other materials may be used.

Figure 3:
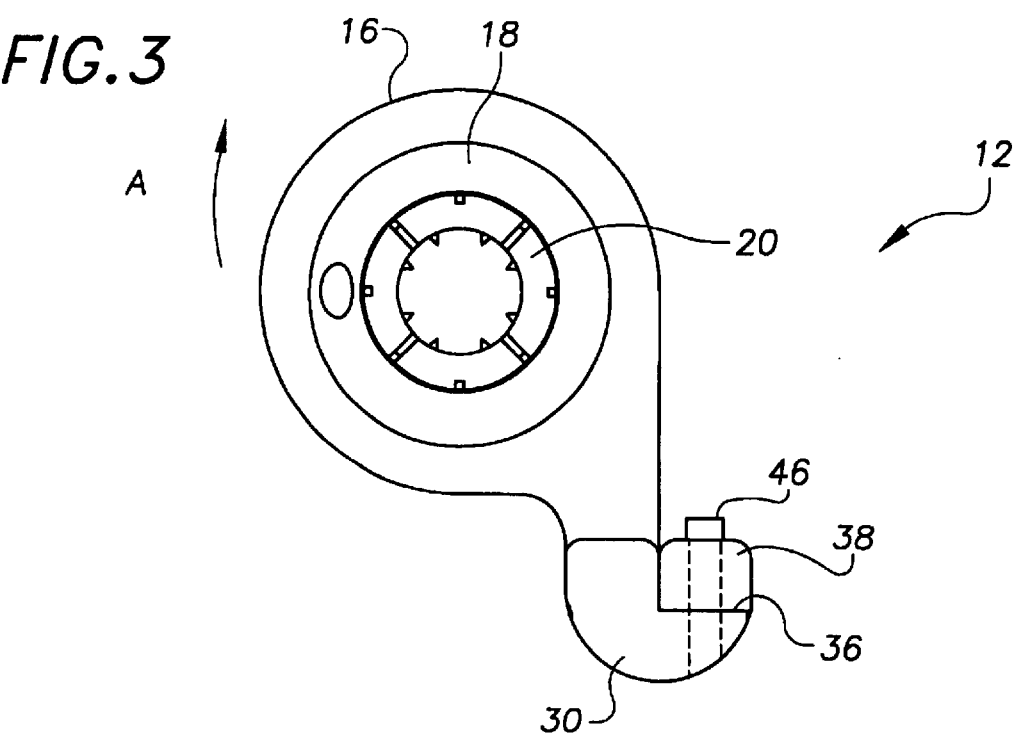
FIG. 3 is an end view of the first bone screw clamp assembly of the apparatus for external fixation of bones shown in FIG. 1 according to the teachings of the preferred embodiment of the present invention.
Figure 4A:
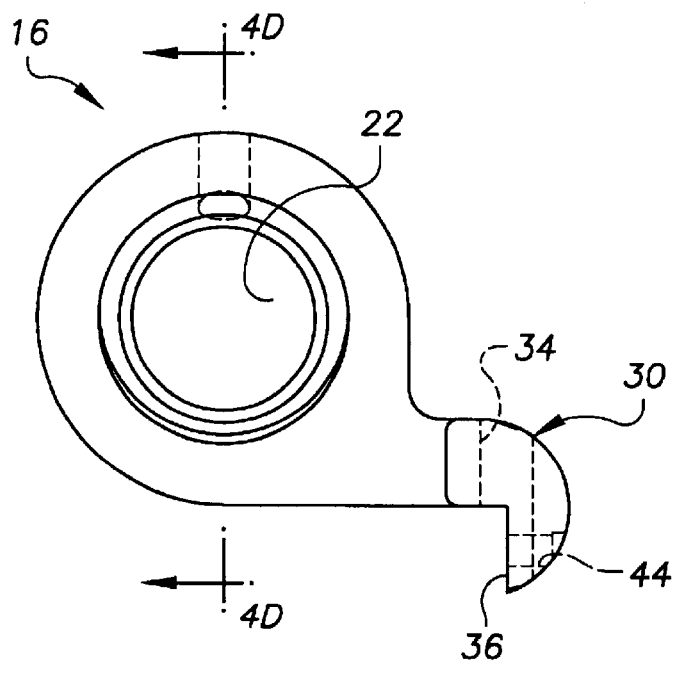
FIGS. 4(A)–4(D) are views of a base of the apparatus for external fixation of bones shown in FIG. 1 according to the teachings of the preferred embodiment of the present invention.
Figure 4B:
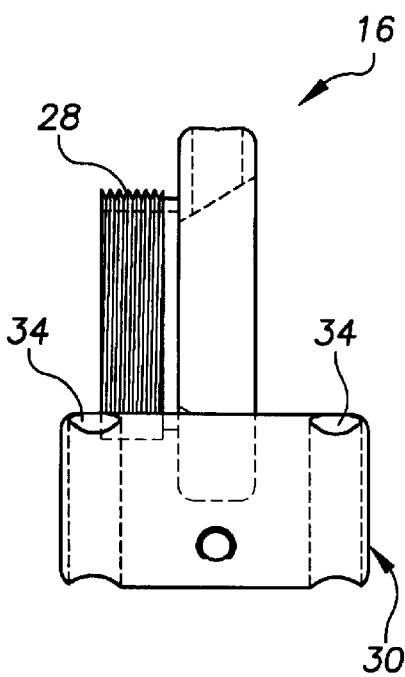
Figure 4C:
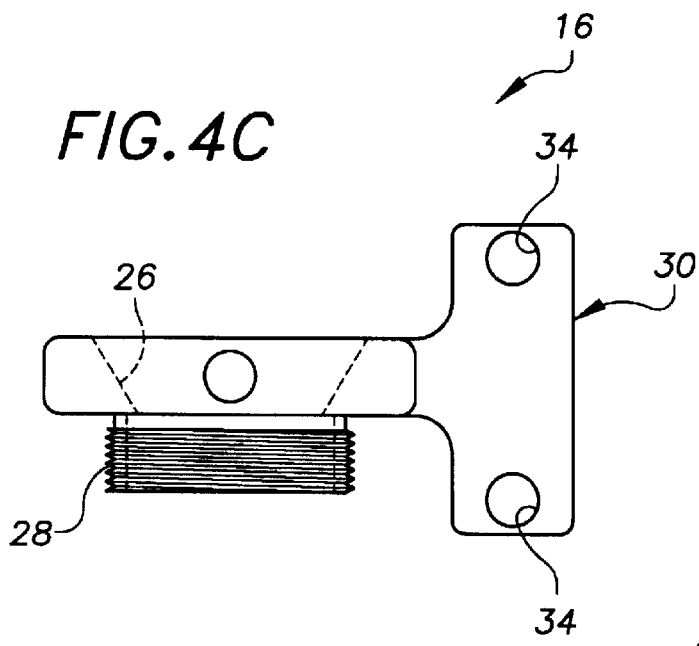
Figure 4D:
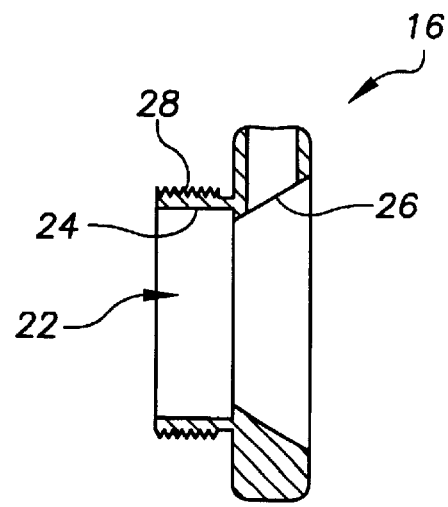

In use, the bone screw clamping assemblies 12 are mounted to the rod 14 for relative universal movement about a point through which the rod 14 passes. In the preferred embodiment, the point 72 is defined by the spherical center of the spherical member 20. The base 16, cap member 18, spherical member 20 and rings 64 cooperate to provide a locking arrangement for precluding relative movement between the bone clamping assembly 12 and the rod 14. Normally, the bone screw clamping assembly 12 is permitted to longitudinally translate along the rod 14 and universally move relative to the rod 14 about the spherical center of the spherical member 20. When the cap member 18 is rotated relative to the base 16 in a first direction (clockwise as shown in FIG. 3), the cap member 18 further threadably engages the base 16 thereby drawing the rings 64 together so as to clamp down on the spherical member 20.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for securing a first bone portion in a fixed relationship to a second bone portion by a first bone screw connected to the first bone portion and a second bone screw connected to the second bone portion, the apparatus comprising:

a longitudinally extending rod defining an axis; and
   a bone screw clamping assembly for receiving the first bone screw, the bone screw clamping assembly mounted to the rod for relative pivotal movement in a plane parallel to the axis and about a point, the rod passing through the point.

2. The apparatus for securing a first bone portion in a fixed relationship to a second bone portion of claim 1, wherein the bone screw clamping assembly includes a locking arrangement for precluding relative movement between the bone screw clamping assembly and the rod.

3. The apparatus for securing a first bone portion in a fixed relationship to a second bone portion of claim 1, wherein the bone screw clamp assembly is mounted to the rod for relative pivotal movement about the point in any direction, the rod passing through the point.

4. The apparatus for securing a first bone portion in a fixed relationship to a second bone portion of claim 3, wherein the bone screw clamp assembly includes a spherical member having an aperture receiving the rod, a center of the spherical member being coincident with the point.

5. The apparatus for securing a first bone portion in a fixed relationship to a second bone portion of claim 1, wherein the bone screw clamping assembly is translatable longitudinally along the axis of the rod.

6. The apparatus for securing a first bone portion in a fixed relationship to a second bone portion of claim 3, wherein the bone screw clamping assembly includes a cap member threadable engageable with a base, the cap member being rotatable in a first direction to preclude relative movement between the bone screw clamping assembly and the rod.

7. The apparatus for securing a first bone portion in a fixed relationship to a second bone portion of claim 6, further comprising a ring disposed between the cap member and the spherical member.

8. The apparatus for securing a first bone portion in a fixed relationship to a second bone portion of claim 1, wherein the bone screw clamping assembly includes a generally cylindrical portion defining an aperture to receive the rod, the aperture including at least a portion having an enlarged end.

9. The apparatus for securing a first bone portion in a fixed relationship to a second bone portion of claim 8, wherein the portion of the aperture conically tapers.

10. An apparatus for securing a first bone portion in a fixed relationship to a second bone portion, the apparatus comprising:

a longitudinally extending rod; and a clamping assembly for receiving the first bone screw, the clamping assembly including a spherical member having a rod aperture passing therethrough and receiving the longitudinally extending rod, the clamping assembly further including a base and a cap member secured to the base, the base and the cap member cooperatively defining a cavity receiving the spherical member such that the base and the cap member universally articulate as a unit about the spherical member in any direction.

11. The apparatus for securing a first bone portion in a fixed relationship to a second bone portion of claim 10, wherein the cap member threadably engages the base.

12. The apparatus for securing a first bone portion in a fixed relationship to a second bone portion of claim 11, wherein rotation of the cap member in a first direction arrest relative movement between the base and the rod.

13. The apparatus for securing a first bone portion in a fixed relationship to a second bone portion of claim 10, wherein the base and cap member universally articulate about a point, the rod passing through the point.

14. The apparatus for securing a first bone portion in a fixed relationship to a second bone portion of claim 10, wherein the clamping assembly is longitudinally translatable along an axis of the longitudinally extending rod.

15. The apparatus for securing a first bone portion in a fixed relationship to a second bone portion of claim 13, wherein a center of the spherical member is coincident with the point.

16. The apparatus for securing a first bone portion in a fixed relationship to a second bone portion of claim 10, further comprising a ring disposed between the cap member and the spherical member.

17. The apparatus for securing a first bone portion in a fixed relationship to a second bone portion of claim 10, wherein the bone screw clamping assembly includes a generally cylindrical portion defining an aperture to receive the rod, the aperture including at least a portion have an enlarged end.

18. The apparatus for securing a first bone portion in a fixed relationship to a second bone portion of claim 13, wherein the portion of the aperture conically tapers.

19. A method of securing a first bone portion in a fixed relationship to a second bone portion by a first bone screw connected to the first bone portion and a second bone screw connected to the second bone portion, the method comprising the steps of:

providing a first clamping assembly receiving the first bone screw, said first clamping assembly including a spherical portion;

providing a second clamping assembly receiving the second bone screw;

connecting the first and second clamping assemblies with a longitudinally extending rod; and pivotally adjusting the first clamping assembly relative to the rod in a plane parallel to an axis defined by and about a point through which the rod passes.

20. The method of securing a first bone portion in a fixed relationship to a second bone portion of claim 19, further comprising the step of longitudinally translating the first clamping assembly along the rod.

21. The method of securing a first bone portion in a fixed relationship to a second bone portion of claim 19, further comprising the step of arresting relative movement between the first clamping assembly and the longitudinally extending rod.

22. The method of securing a first bone portion in a fixed relationship to a second bone portion of claim 21, wherein the first clamping assembly includes a base and cap member threadably engaging the base and wherein the step of arresting relative movement between the first clamping assembly and the longitudinally extending rod includes the step of rotating the cap member relative to the base.

23. The method of securing a first bone portion in a fixed relationship to a second bone portion of claim 19, wherein the first clamping assembly further includes a spherical member and wherein the step of pivotally adjusting the first clamping assembly relative to the rod includes the step of articulating the first clamping assembly about a center of the spherical member.

24. The method of securing a first bone portion in a fixed relationship to a second bone portion of claim 22, wherein the first clamping assembly includes a spherical member disposed in a cavity defined by the base and the cap member and wherein the step of arresting relative movement between the first clamping assembly and the rod includes the step of compressing the spherical member.

* * * * *

UNITED STATES PATENT AND TRADEMARK OFFICE
CERTIFICATE OF CORRECTION

PATENT NO. : 6,482,206 B2
DATED : November 19, 2002
INVENTOR(S) : Ryan J. Schoenefeld It is certified that error appears in the above-identified patent and that said Letters Patent is hereby corrected as shown below:

Column 1,
Line 61, "limited" should be -- limit --.

Column 3,
Line 19, "appreciated" should be -- appreciate --.

Column 4,
Line 61, "threadable" should be -- threadably --.

Column 5,
Line 50, "have" should be -- having --.

Column 6,
Line 2, "claim 13" should be -- claim 17 --.

Signed and Sealed this

Twelfth Day of August, 2003

JAMES E. ROGAN
*Director of the United States Patent and Trademark Office*